United States Patent
Mao

(10) Patent No.: US 9,943,258 B2
(45) Date of Patent: Apr. 17, 2018

(54) SAFETY BLOOD-COLLECTION NEEDLE

(71) Applicant: Shanghai Jinta Medical Co., Ltd., Shanghai (CN)

(72) Inventor: Chunyuan Mao, Shanghai (CN)

(73) Assignee: Shanghai Jinta Medical Co., Ltd., Shanghai (CN)

( * ) Notice: Subject to any disclaimer, the term of this patent is extended or adjusted under 35 U.S.C. 154(b) by 0 days.

(21) Appl. No.: 15/025,943

(22) PCT Filed: Jun. 23, 2014

(86) PCT No.: PCT/CN2014/080490
§ 371 (c)(1),
(2) Date: Mar. 30, 2016

(87) PCT Pub. No.: WO2015/154336
PCT Pub. Date: Oct. 15, 2015

(65) Prior Publication Data
US 2017/0014062 A1    Jan. 19, 2017

(30) Foreign Application Priority Data

Apr. 11, 2014  (CN) .......................... 2014 1 0143343
Apr. 11, 2014  (CN) ...................... 2014 2 0173152 U

(51) Int. Cl.
*A61B 5/15*   (2006.01)
*A61B 5/153*  (2006.01)

(52) U.S. Cl.
CPC ........ *A61B 5/150664* (2013.01); *A61B 5/153* (2013.01); *A61B 5/15003* (2013.01);
(Continued)

(58) Field of Classification Search
CPC .. A61B 5/150732; A61B 5/150633–5/150656; A61B 5/150206; A61B 5/150839
(Continued)

(56) References Cited

U.S. PATENT DOCUMENTS 4,943,283 A * 7/1990 Hogan ................. A61M 5/158
                                                             604/198
6,264,619 B1 * 7/2001 Ferguson ........... A61B 5/15003
                                                             206/569
(Continued)

FOREIGN PATENT DOCUMENTS

CN    201453283 U    5/2010
CN    201642029 U    11/2010
(Continued)

OTHER PUBLICATIONS

International Search Report from PCT/CN2014/080490 dated Jan. 8, 2015.
(Continued)

*Primary Examiner* — Michael C. Stout
(74) *Attorney, Agent, or Firm* — Andrus Intellectual Property Law, LLP

(57) ABSTRACT

A safety blood-collection needle, comprising a needle base, a needle hub, a flexible tube, a straight needle, a straight needle shaft, and a needle head; the safety blood-collection needle further comprises a protective cover, a slider, a handle, and a position limiting mechanism; one end of the needle base is fixed and is in communication with the needle head; the slider movably sleeved on the needle base; the position limiting mechanism is arranged on the slider and needle base. The slider is arranged on the needle base and slides in order to cover the needle head, so that safety is greatly increased when handling the needle head following blood collection; the use of a spring-type needle head is avoided, thus reducing the suffering of the patient.

13 Claims, 2 Drawing Sheets

(52) U.S. Cl.
CPC .... *A61B 5/15074* (2013.01); *A61B 5/150259* (2013.01); *A61B 5/150389* (2013.01); *A61B 5/150519* (2013.01); *A61B 5/150633* (2013.01); *A61B 5/150717* (2013.01); *A61B 5/150732* (2013.01)

(58) Field of Classification Search
USPC ........................................................ 600/577
See application file for complete search history.

(56) References Cited

U.S. PATENT DOCUMENTS

| | | | |
|---|---|---|---|
| 2002/0099340 A1 | 7/2002 | Crawford et al. | |
| 2003/0060772 A1* | 3/2003 | Swenson | A61M 5/321 604/183 |
| 2003/0176842 A1* | 9/2003 | Wilkinson | A61M 5/3243 604/263 |
| 2003/0208160 A1* | 11/2003 | Crawford | A61B 5/15003 604/164.08 |
| 2004/0236287 A1* | 11/2004 | Swenson | A61M 5/3245 604/263 |

FOREIGN PATENT DOCUMENTS

| | | |
|---|---|---|
| CN | 202446098 U | 9/2012 |
| CN | 202723859 U | 2/2013 |
| CN | 203828943 U | 9/2014 |
| CN | 203828945 U | 9/2014 |
| CN | 104274190 A | 1/2015 |
| CN | 104274190 B | 5/2015 |
| EP | 2255728 A1 | 12/2010 |
| JP | 2002325752 A | 11/2002 |
| JP | 2003265610 A | 9/2003 |
| JP | 6169794 B2 | 7/2017 |
| WO | 2012009599 A1 | 1/2012 |

OTHER PUBLICATIONS

Written Opinion Report from PCT/CN2014/080490 dated Jan. 8, 2015.
First Office Action from the Chinese priority patent application CN201410143343.3 dated Feb. 15, 2016.
First Office Action from the Japanese patent application JP2016524517 dated Mar. 14, 2017.

* cited by examiner

SAFETY BLOOD-COLLECTION NEEDLE

CROSS REFERENCE TO RELATED APPLICATIONS

The present application is the U.S. national stage application of International Application PCT/CN2014/080490, filed Jun. 23, 2014, which international application was published on Oct. 15, 2015, as International Publication WO2015/154336. The International Application claims priority of Chinese Patent Application No. 201410143343.3, filed Apr. 11, 2014, and Chinese Patent Application No. 201420173152.7, filed Apr. 11, 2014, the contents of which are incorporated herein by reference in their entireties.

FIELD OF INVENTION

The present invention relates to a blood collecting needle, particularly to a safety blood-collection needle.

PRIOR ARTS

Blood collecting and testing technology has already been quite mature, but it can not yet achieve the goal of arriving at a conclusion without collecting blood from patient, and the surgeon need to use blood collecting needle and blood collecting hose to finish initial process of blood tests. Therefore, blood collecting needle is now one of the largest selling medical equipment products in the world. However, it is noteworthy that needle body injury accident happens millions of times each year in the hospitals of the world because of the broken needle head or the improper operation of medical staff. Based on the statistical data issued by American Medical Association, the accident that medical staff are needlestick injury happens about one million times each year only in US, wherein at least one thousand people will be infected with virus such as hepatitis B, hepatitis C and HIV attached to the needle heads. The medical expense for each first aid and treatment of those medical staff and patients stuck to injury by broken needles is 3000 dollars per capita.

Since domestic and foreign companies have made efforts to develop safe blood collecting devices, there are various safety blood-collection needles in the market. These safe blood collecting devices have many disadvantages, including: high manufacture cost, complex manufacture process, difficulty to ensure manufacture quality, verbose operation for medical staff and difficulty to ensure safety.

At present, to the commonly-used disposable blood collecting needle, it is needed to cover the needle head with the needle guard before use, to protect the needle head, for example, to prevent the needle head from bending or crushing. In use, when the needle guard is removed, it is prone to cause needlestick injury accident. However, the real danger happens in the disposal phase after blood collection is completed. After the needle is pulled out from the patient body and ready to be disposed, it is easy to be stuck to injury no matter the needle is either placed in the special disposing box or put on a needle cover, resulting in severe consequences such as infection of the medical staff.

In view of this disadvantage, some blood collecting needles employ retractable needle head. After the blood collection is completed, the needle head retracts to a protective cover by elastic force of spring configuration. Thus, although this solution can effectively protect needle head and prevent the medical staff from injuring, it will cause great pain of patient because of mechanical motion of the needle head retraction.

On the other hand, at the other end of the blood collecting hose, a straight needle for inserting within vacuum tube is normally bared in use, lowering operation safety.

Content of the Present Invention

In view of the technical problems to be solved, the present invention provides a blood collecting needle with higher safety and less pain of patients to overcome disadvantages of prior art including lower safety and increased pain of the patients.

The following technical solutions are provided to solve the above technical problems:

a safety blood-collection needle, comprising: a needle seat, a needle guard, a hose, a straight needle, a straight needle handle and a needle head, the needle guard covering the needle head, two ends of the hose communicating with the straight needle and the needle seat, the straight needle handle disposed on a joint of the straight needle and the hose, the straight needle used to be inserted into a vacuum tube, characterized in that, the safety blood-collection needle further comprises a protective shield, a slider, a handle and a retaining mechanism, the needle seat being cylindrical, which is fixed to and communicates with the needle head at one end and connects to the hose at the other end;

the slider is a cylinder having two opened ends and movably covers the needle seat, and the length of the slider in a movable direction is larger than the length of the needle head;

the axial length of the needle seat is larger than the length of the needle head;

the retaining mechanism is disposed on the slider and the needle seat, for securing the slider on the needle seat after the slider slides to a position where the slider completely shelters the needle head;

the handle is fixed to the needle seat, the handle abuts against the slider;

the inner diameter of the protective shield is larger than the outer diameter of the vacuum tube, and the protective shield covers the straight needle and is fixed to the straight needle handle by screwing. Herein, the hose is commonly-used hose for blood transfusion in the field of medical product, and the description thereof is omitted.

That is, to the blood collecting needle of the present invention, the needle seat is longer than the needle head. In this way, the above cylindrical slider can slide back and forth on the needle seat, making the needle head switch its status between sheltered by the slider and exposed completely. The retaining mechanism is used to restrain the movement of the slider.

In use, under initial status where the slider is fixed to the needle seat by the retaining mechanism, (i.e. the state where the needle head is completely exposed), the needle guard is removed and blood is collected; after the blood collection is completed, the fixation of the slider with the needle seat is released, and the slider slides towards the needle head until the slider completely shelters the needle head, at this time the slider is fixed on the needle seat once again (by the retaining mechanism). Since the needle head is sheltered without putting on the needle guard once again, the safety is improved greatly.

In addition, the handle is fixed on the needle seat, on one hand, the user can grasp the handle in operation, on the other hand, the handle abuts against the slider, so that both the handle and the slider can be pressed with only one thumb to conduct movable operation, making the operation thereof more convenient than the present blood collecting needle.

Furthermore, the protective shield covers the straight needle, this configuration of which can effectively isolate the straight needle when it is exposed, to prevent safety accident.

Preferably, the retaining mechanism includes a first elastic washer and two second elastic washers;

the first elastic washer is adhered to the inner periphery of one end of the slider near the hose, and the edge of the first elastic washer smoothly is adhered to the inner wall of the slider;

the two second elastic washers are engaged with the needle seat by means of covering and are adhered to the needle seat, when the slider slides to a position where it completely shelters the needle head or a position where the needle head is completely exposed, the second elastic washers are engaged with the first elastic washer to limit the movement of the slider.

That is, when the slider slides toward the needle head to a position where it completely shelters the needle head or a position where the needle head is exposed, in order to secure the slider to the needle seat, the second elastic washers serving as the retaining mechanism and located on the outer periphery of the needle seat are fixed to the first elastic washer on the inner periphery by engagement. Since the first elastic washer smoothly is adhered to the inner wall of the slider, the first elastic washer can be smoothly pushed to a position where it engages with the second elastic washers.

Preferably, the retaining mechanism includes an elastic fastener and two slots;

the two slots are disposed on the needle seat, and the elastic fastener is disposed on the slider, when the slider slides to a position where it completely shelters the needle head or a position where the needle head is completely exposed, the two slots are used to engage with the elastic fastener to limit the movement of the slider.

That is, the slider can slide axially along the needle seat, when needing to collect blood, the elastic fastener on the slider engages with the slot on the needle seat near one end of the needle seat, to completely expose the needle head. When blood collection is completed and the needle head needs to be sheltered, the slider slides to a position where the elastic fastener engages with the slot on other end of the needle seat, to shelter the needle head. Herein, the elastic fastener refers to a fastener which uses elastic force to maintain engagement, and said engagement can be released by applying an external force larger than the elastic force.

Preferably, the safety blood-collection needle further includes a protective cover;

the protective cover covers and is engaged with and is secured to the needle seat, and the protective cover, together with the needle seat, surround and form a cavity to accommodate the slider;

the handle is integrally formed on the protective cover.

That is, further providing a protective cover functioning as a connector to protect the communication between the needle seat and the hose. The handle is secured to the needle seat indirectly by being provided on the protective cover.

Preferably, the protective cover is secured to the outer periphery of one end of the needle seat by screwing. This configuration allows more secure fixation between the protective cover and the needle seat. Furthermore, the protective cover can protect the slider.

Preferably, the slider is provided with at least one anti-slip area. Herein, the purpose of the anti-slip area is to make hands have more frictional force when pushing the slider. For example, artisan can wrap the slider with high friction factor rubber material or shape certain area on the slider as undulation/groove shape to increase contact area of the slider with respect to fingers.

Preferably, the slider is made by elastic material, and the slider integrates with the elastic fastener, and the needle seat integrates with the slots, and the slider is provided with several hollowed-out areas thereon.

The purpose of providing the hollowed-out areas is to make the operator observe the position of the needle head by naked eye even under the condition where the slider shelters the needle head, thereby ensuring operation safety. On the other hand, when the first elastic fastener integrates with the slider, the hollowed-out areas provide motion space for the first elastic fastener.

The advantageous effects of the present invention lie in: by the slider provided to slide on the needle seat to shelter the needle head, the safety for treatment of the needle head after blood collection is increased drastically; pain of the patient is alleviated because of avoiding the use of spring-type needle head.

DETAILED DESCRIPTION OF THE PREFERRED EMBODIMENT

The following examples further illustrate the present invention, but the present invention is not limited thereto.

With reference to the Figures, preferred embodiments are provided to illustrate technical solution of the present invention. However, it does not mean to limit the present invention within the scope of these embodiments.

Figure 1:
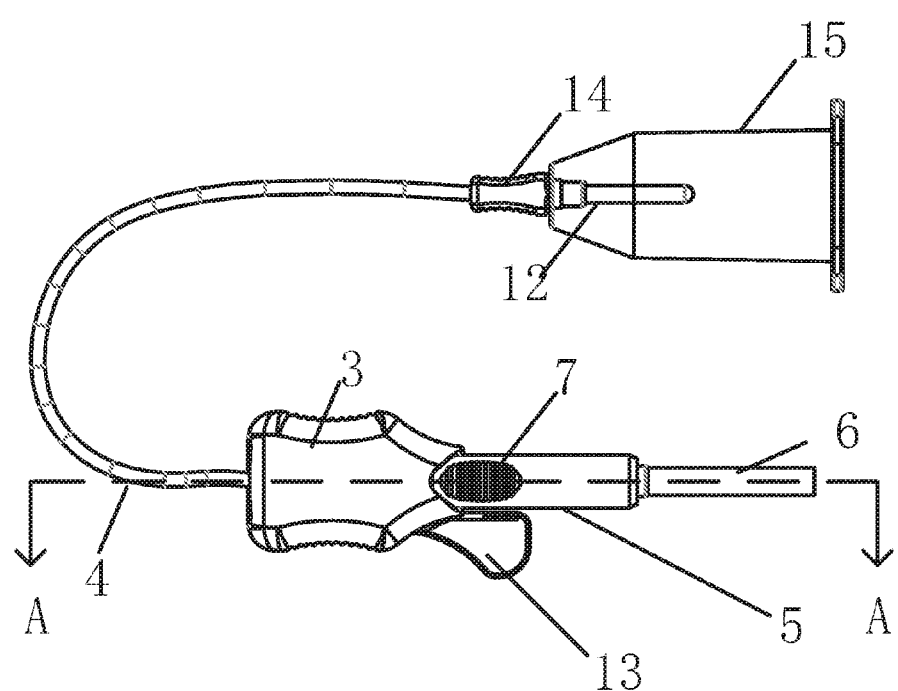
FIG. 1 is a structural schematic showing a safety blood-collection needle according to a preferred embodiment of the present invention.
Figure 2:
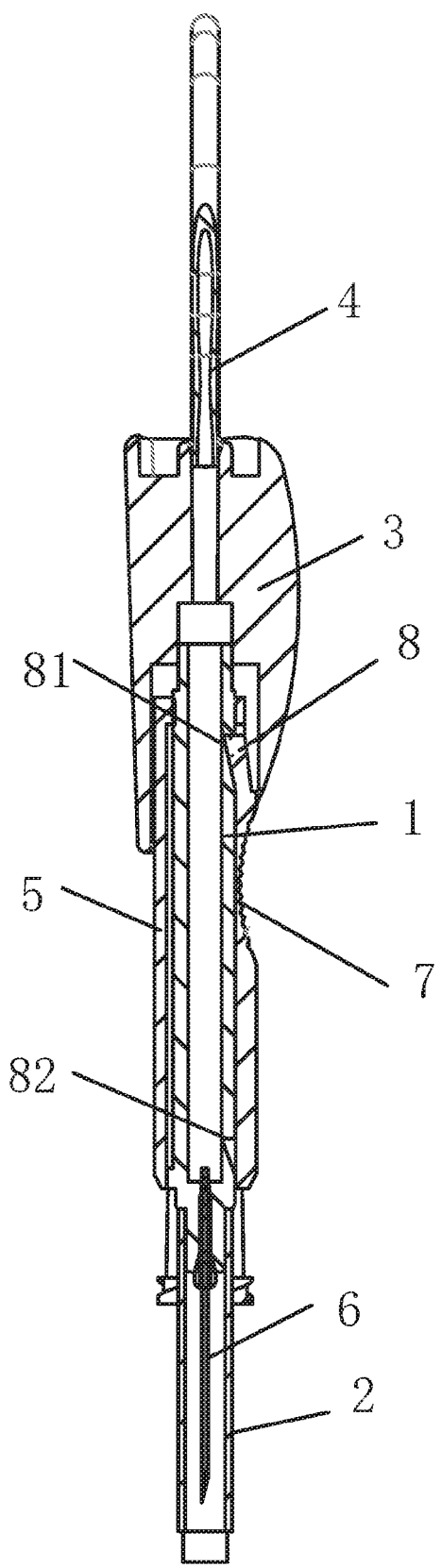
FIG. 2 is a sectional view taken along line A-A in FIG. 1.

Various embodiments are provided to illustrate the present invention. However, it does not mean to limit the present invention within the scope of these embodiments. FIG. 1 is a structural schematic showing a safety blood-collection needle according to the present embodiment and FIG. 2 is a sectional view taken along line A-A in FIG. 1. As shown in FIGS. 1-2, a safety blood-collection needle according to the present embodiment includes a needle seat 1, a needle guard 2, hose 4, a straight needle 12, a handle 13, a straight needle handle 14, a protective shield 15, a protective cover 3, needle head 6 and slider 5, and the needle guard 2 covers the needle head 6, and the needle seat 1 is a cylinder having two opened ends, and one end of the needle seat 1 communicates with the hose 4 through the protective cover 3, and the other end of the needle seat 1 is provided with the needle head 6. Two ends of the hose 4 communicate with the straight needle 12 and the needle seat 1 respectively.

The straight needle handle 14 is disposed at the connection between the straight needle 12 and the hose 4, and the straight needle 12 is inserted into a vacuum tube.

The slider 5 is a cylinder having two opened ends and covers the needle seat 1 movably, and the length of the slider 5 in a movable direction is larger than the length of the needle head 6.

The axial length of the needle seat 1 is larger than the length of the needle head 6.

The protective cover 3 is engaged with the needle seat 1 by means of covering and is secured to the needle seat 1, and the protective cover 3, together with the needle seat 1, surround and form a cavity to accommodate the slider 5.

The handle 13 is integrally formed on the protective cover 3. The handle 13 abuts against the slider 5.

The inner diameter of the protective shield 15 is larger than the outer diameter of the vacuum tube. The protective shield 15 covers the straight needle 12 and is fixed on the straight needle handle 14 by screwing.

The safety blood-collection needle according to the present embodiment further includes a retaining mechanism, and the retaining mechanism includes an elastic fastener 8 and a plurality of slots 81, 82.

the plurality of slots 81, 82 are disposed on the needle seat 1, and the elastic fastener 8 is disposed on the slider 5, when the slider 5 slides to a position where it completely shelters the needle head 6 or a position where the needle head 6 is completely exposed, the plurality of slots 81, 82 are used to engage with the elastic fastener 8 to limit the movement of the slider 5.

A passage is formed in the protective cover 3, in which one end of the passage is fixed to outer periphery of one end of the needle seat 1 away from the needle head 6 by screwing, and the other end of the passage communicates with the hose 4.

Furthermore, the slider 5 is provided with anti-slip area 7, which is a groove-shape configuration with serrate pattern inside, thereby facilitating pushing the slider 5 by fingers while increasing contact area.

The slider 5 is made by elastic material, which integrates with the elastic fastener 8, and the protective cover 3 integrates with the plurality of slots 81, 82, the slider 5 is provided with several hollowed-out areas (not shown in Figures) thereon.

In the safety blood-collection needle of the present embodiment, the needle seat 1 is longer than the needle head 6. In this way, the cylindrical slider 5 can slide back and forth on the needle seat 1, to switch between a status in which the needle head 6 is sheltered by the slider 5 and a status in which the needle head 6 is completely exposed.

In use, under an initial status where the slider is fixed to the needle seat 1 by engagement of the slot 81 and the elastic fastener 8, (a status where the needle head 6 is completely exposed), the needle guard 2 is removed and blood is collected; after the blood collection is completed, the fixation of the slider 5 with the needle seat 1 is released, and the slider 5 slides towards the needle head 6 until the slider 5 completely shelters the needle head 6 (as shown in FIGS. 1-2), at this time the slider 5 is fixed on the needle seat 1 once again (by engagement of the slot 82 and the elastic fastener 8). In this way, since the needle head 6 can be sheltered without putting on the needle guard 2 once again, the safety is improved greatly.

Although the present invention has been described with reference to certain preferred version thereof, other versions and variations are possible and contemplated. Those skilled in the art should appreciate that they can readily use the disclosed conception and specific embodiments as a basis for designing or modifying other structures for providing the same purposes of the present invention without departing from the spirit and scope of the invention as defined by the following claims. For example, instead of the engagement structure such as the elastic fastener and the plurality of slots, an elastic washer can be employed to fasten the slider on the needle seat, these variation and modification fall into the scope of the present invention. Therefore, the protection scope of the present invention is defined by claims.

What is claimed is:

1. A safety blood-collection needle, comprising:
    a needle seat having a plurality of slots, a needle guard, a hose, a straight needle, a straight needle handle and a needle head, the needle guard covering the needle head, two ends of the hose communicating with the straight needle and the needle seat, respectively, the straight needle handle being disposed on a joint between the straight needle and the hose, and the straight needle being configured to be inserted into a vacuum tube, wherein the needle seat is cylindrical and communicates with the needle head at a first end of the needle seat, and communicates with the hose at a second end of the needle seat;
    a protective shield, a slider, a protective cover, a handle, and a retaining mechanism, wherein the slider is a cylinder having two opened ends and is configured to movably cover the needle seat, wherein the length of the slider in a movable direction is larger than the length of the needle head, wherein the axial length of the needle seat is larger than the length of the needle head, wherein the retaining mechanism is positioned between the protective cover and the needle seat such that the slider is secured to the needle seat when the slider is in a first position in which the slider completely shelters the needle head and wherein the slider is secured to the needle seat when the slider is in a second position in which the needle head is completely exposed, each by engagement between the retaining mechanism and the plurality of slots;
    wherein the handle is fixed to the needle seat and the handle abuts against the slider, wherein the inner diameter of the protective shield is larger than the outer diameter of the vacuum tube, wherein the protective shield covers the straight needle, and wherein the protective shield is fixed to the straight needle handle.

2. The safety blood-collection needle according to claim 1, wherein the retaining mechanism includes a first elastic washer and two second elastic washers, wherein the first elastic washer is adhered to the inner periphery of the inner wall of the slider, and wherein the two second elastic washers are adhered to and are located on the outer periphery of the needle seat, wherein the slider is slidable between the first position and the second position, and wherein one of the two second elastic washers engage with the first elastic washer to limit the movement of the slider when the slider is in the second position.

3. The safety blood-collection needle according to claim 2, wherein the first elastic washer and the two second elastic washers are disposed within the plurality of slots.

4. The safety blood-collection needle according to claim 1, wherein the protective cover covers and is secured to the needle seat, wherein the protective cover, together with the needle seat, surround and form a cavity to accommodate the slider, and wherein the handle is integrally formed on the protective cover.

5. The safety blood-collection needle according to claim 4, wherein the protective cover is removably secured to the outer periphery of the second end of the needle seat that communicates with the hose.

6. The safety blood-collection needle according to claim 1, wherein the slider is provided with at least one anti-slip area.

7. The safety blood-collection needle according to claim 1, wherein the slider is made by elastic material and the slider includes an elastic fastener, wherein the elastic fastener removably engages with the plurality of slots in the needle seat to limit the movement of the slider past the first position relative to the second position and past the second position relative to the first position.

8. The safety blood-collection needle according to claim 5, wherein the protective cover is removably secured to the needle seat via threads.

9. A safety blood-collection needle, comprising:
a needle seat, a needle guard, a hose, a straight needle, a straight needle handle and a needle head, the needle guard covering the needle head, two ends of the hose communicating with the straight needle and the needle seat, respectively, the straight needle handle being disposed on a joint of the straight needle and the hose, the straight needle used to be inserted into a vacuum tube, characterized in that, the safety blood-collection needle further comprises a protective shield, a slider, a handle and a retaining mechanism, the needle seat being cylindrical, the needle seat being fixed to and communicating with the needle head at a first end of the needle seat and to the hose at a second end of the needle seat;
wherein the slider is a cylinder having two opened ends and is configured to movably cover the needle seat, wherein the length of the slider in a movable direction is larger than the length of the needle head, and wherein the axial length of the needle seat is larger than the length of the needle head;
wherein the retaining mechanism is disposed on the slider and the needle seat, for securing the slider on the needle seat after the slider is in a first position where the slider completely shelters the needle head, wherein the retaining mechanism includes a first elastic washer and two second elastic washers, wherein the first elastic washer is adhered to the inner periphery of one end of the slider near the hose, and wherein an edge of the first elastic washer is adhered to the inner wall of the slider;
wherein the handle is fixed to the needle seat and the handle abuts against the slider, wherein the inner diameter of the protective shield is larger than the outer diameter of the vacuum tube, the protective shield is configured to cover the straight needle and is fixed to the straight needle handle by threads; and
wherein the two second elastic washers are adhered to and engaged with the needle seat so as to encircle the needle seat when the slider is in the first position where the slider completely shelters the needle head, and where the two second elastic washers engage with the first elastic washer to limit the movement of the slider when the slider is in the second position where the needle head is completely exposed.

10. The safety blood-collection needle according to claim 9, further comprising a protective cover that covers, is engaged with, and is secured to the needle seat, wherein the protective cover, together with the needle seat, surround and form a cavity to accommodate the slider, and wherein the handle is integrally formed on the protective cover.

11. The safety blood-collection needle according to claim 10, wherein the protective cover is removably secured to the outer periphery of the second end of the needle seat connected to the hose.

12. The safety blood-collection needle according to claim 9, wherein the slider is provided with at least one anti-slip area.

13. The safety blood-collection needle according to claim 9, wherein the protective cover is removably secured to the needle seat via threads.

* * * * *